(12) United States Patent
Szilvassy et al.

(10) Patent No.: US 7,767,694 B2
(45) Date of Patent: Aug. 3, 2010

(54) PHARMACEUTICAL COMPOSITION HAVING PROKINETIC EFFECT

(75) Inventors: Zoltan Szilvassy, Debrecen-Józsa (HU); Altila Kolonics, Budapest (HU); Kálmán Tory, Budapest (HU); Peter Literatinagy, Budapest (HU)

(73) Assignee: N-Gene Research Laboratories Inc., New York, NY (US)

( * ) Notice: Subject to any disclaimer, the term of this patent is extended or adjusted under 35 U.S.C. 154(b) by 0 days.

(21) Appl. No.: 12/320,819

(22) Filed: Feb. 5, 2009

(65) Prior Publication Data

US 2009/0149498 A1 Jun. 11, 2009

Related U.S. Application Data

(63) Continuation of application No. 11/629,280, filed as application No. PCT/IB2005/001637 on Jun. 13, 2005, now abandoned.

(30) Foreign Application Priority Data

Jun. 14, 2004 (HU) ....................... 401176

(51) Int. Cl.
  *A61K 31/4406* (2006.01)
  *A61K 31/4453* (2006.01)
(52) U.S. Cl. ..................................... 514/318
(58) Field of Classification Search ........................ None
  See application file for complete search history.

(56) References Cited

U.S. PATENT DOCUMENTS 4,187,220 A 2/1980 Takacs et al.

OTHER PUBLICATIONS

Thompson et al., Transplant. Proceedings, (Jul.-Aug. 2006), 38(6), 1838-9.*
Madacsy et al., Digestive Diseases and Sciences, vol. 47, No. 9, Sep. 2002, p. 1975-1981.
Sari et al., Gastroenterology, vol. 116, No. 4, Part 2, Apr. 1999, p. A30, Abstract only.
Worker, IDRUGS, Current Drugs Ltd., GB, vol. 2, No. 9, 1999, pp. 859-860.
Hamel et al. Experimental Physiology, 93/1 (2007) pp. 116-120.

* cited by examiner

*Primary Examiner*—Phyllis G. Spivack
(74) *Attorney, Agent, or Firm*—Birch, Stewart, Kolasch & Birch, LLP

(57) ABSTRACT

The present invention is directed to a method of treating gastrointestinal motility disorders in a subject in need thereof which includes: administering a therapeutically effective amount of O-(3-piperidino-2-hydroxypropyl) nicotinic amidoxime or a pharmaceutically suitable acid addition salt thereof, wherein the gastrointestinal motility disorders include reflux esophagitis, type II biliary and pancreatic sphincter of Oddi dysfunction, type III biliary and pancreatic sphincter of Oddi dysfunction, postcholecystectomy syndrome, non-ulcerative colitis or fecal incontinences.

7 Claims, No Drawings

PHARMACEUTICAL COMPOSITION HAVING PROKINETIC EFFECT

This application is a Continuation of application Ser. No. 11/629,280 filed on Jul. 25, 2007 now abandoned and for which priority is claimed under 35 U.S.C. §120, which is the National Stage of PCT/IB2005/001637 filed Jun. 13, 2005, which claims the benefit of priority of Application No. P0401176 filed in Hungary on Jun. 14, 2004 under 35 U.S.C. §119; the entire contents of all are hereby incorporated by reference.

FIELD OF THE INVENTION

The invention refers to a pharmaceutical composition having prokinetic effect. More specifically, the invention refers to the use of O-(3-piperidino-2-hydroxy-1-propyl)nicotinic amidoxime or a pharmaceutically suitable acid addition salt thereof for the preparation of a pharmaceutical composition that restores and/or enhances the activity of the neuronal nitric oxide synthase enzyme.

BACKGROUND OF THE INVENTION

Nitric oxide is a ubiquitous signal transducer molecule having very significant regulatory roles. Nitric oxide is produced from L-arginine by at least three different enzymes [neuronal nitric oxide synthase (nNOS), inducible nitric oxide synthase (iNOS) and endothelial nitric oxide synthase (eNOS)]. Neuronal type nitric oxide synthase is predominantly expressed in specific neurons of the brain, in non-adrenergic, non-cholinergic autonomic nerve cells, in muscles and in the macula densa region of the renal tubules, however, it is present at lower level in many other tissues as well. In the activation of nNOS enzyme, elevation of intracellular $Ca^{++}$ concentration and protein phosphorylation plays an immediate role. Furthermore, recent observations have revealed that the alteration of the expression level of the enzyme has a significant effect on the regulation of the activity thereof, too [Sasaki, M. et al., Proc. Natl. Acad. Sci. USA 97, 8617 (2000)].

The examination of nNOS knockout animals revealed a series of disease conditions where impaired nNOS enzyme function had significant role in the pathogenesis [Mashimo, H., Am. J. Physiol., 277, 745 (1999)]. The proper motility of the whole gastrointestonal tract, especially the relaxation of sphincters, depends on the activation of nNOS in non-adrenergic, non-cholinergic neurons [Takahashi, T., J. Gastroenterol., 38, 421 (2003)]. Nitric oxide produced by the nNOS enzyme regulates the muscle tone of the sphincter in the lower esophagus, pylorus, anus and the sphincter of Oddi through the inhibition of contraction. The diminished relaxation of sphincters disturbs the function, in this way e.g. the insufficient relaxation of pylorus (or pyloric sphincter) disturbs the coordinated mechanism of gastric emptying. For example, in nNOS knockout mice, gastric dilatation and stasis develop due to the long evacuation of the stomach. A consequence of insufficient nNOS enzyme activity in the sphincter of Oddi is the syndrome of "lazy gall bladder". Owing to the lack of nitric oxide, the relaxation of the sphincter of Oddi is not sufficient resulting in an inhibited flow of bile from the gall bladder which leads to digestive troubles due to acholia as well as to cholecystectasia and cholestasis. The consequence of the latter symptoms is an enhanced risk of inflammatory diseases and formation of gallstones. Since bile plays an essential role in the lipid metabolism, the reduced bile secretion results in higher cholesterol level in the blood, too.

Nitric oxide formation mediated by the nNOS enzyme has an essential role also in the regulation of the urinary bladder. The unsufficient expression and activity of the enzyme may be a cause of urinary retention.

In a similar way, the enzyme plays a fundamental role in the erection of penis [Cuevas A. J. et al, Biochem. Biophys. Res. Commun., 312, 1202], therefore, the unsufficient activity of nNOS enzyme is a frequent cause of erectile disfunctons.

The nNOS enzyme activity has an essential role in normal muscle function partly by attenuating vasoconstriction, thus, allowing adequate blood supply. Recent data indicate that in certain muscle degenerations, for example in Duchene muscular distrophy, also the function of nNOS enzyme is damaged [S. Froehner, Trends in Molecular Medicine, 8, 51 (2002)].

The unsufficient function of nNOS enzyme can be responsible also for diseases related to aggressive behaviour since animal studies indicate that diminished expression and function of the enzyme result in serotonin dysfunction (descreased serotonin turnover, deficient serotonin receptor function) leading to aggressive behaviour [Chiavegatto, S. et al., Proc. Natl. Acad. Sci. USA, 98, 1277 (2001)], Based on experimental observations, the suitable activity of the enzyme is essential for recovery in traumatic peripheral nerve lesion, too [Keilhoff, G. Et al., Cell. Mol. Biol., 49, 885 (2003)]. Recent observations in animals indicate that the reduction of enzyme expression and function significantly contributes to the progression of certain renal diseases (nephrosis, renal damage) [Ni, Z. and Vaziri, N., Biochim. Biophys. Acta, 1638:129 (2003)].

There is no drug presently available that could induce the expression and activity of the nNOS enzyme in different tissues. Although there are partially efficient therapies for the treatment of the listed diseases accompanied by reduced nNOS enzyme activity, but none of them aim at the restoration of the enzyme activity.

O-(3-piperidino-2-hydroxy-1-propyl)nicotinic amidoxime is known from U.S. Pat. No. 4,308,399. According to this document, the compound can be used for the treatment of diabetes angiopathy i.e. a vascular complication of diabetes.

It is know from U.S. Pat. No. 6,306,878 that hydroximic acid derivatives, especially O-(3-piperidino-2-hydroxy-1-propyl)-nicotinic amidoxime, protect the mitochondrion from damages and can be employed for the treatment of diseases that develop through the damage of mitochondrion. The latter diseases include especially neurodegenerative ones such as Parkinson's disease and myopathies such as cardiomyopathy.

From WO 97/23198 it is known that O-(3-piperidino-2-hydroxy-1-propyl)nicotinic amidoxime protects the skin surface from the damaging effect of ultraviolet radiation, and the development of precancerous skin conditions can be inhibited by using the compound.

According to WO 98/58675 and WO 98/58676, O-(3-piperidino-2-hydroxypropyl)nicotinic amidoxime reduces the toxic side-effect of known antiviral and antitumor agents, respectively.

In accordance with WO 00/07580, O-(3-piperidino-2-hydroxypropyl)nicotinic amidoxime can be used for the treatment of autoimmune diseases such as type I diabetes mellitus (insulin-dependent diabetes mellitus, IDDM).

It is known from WO 03/007951 that D-(3-piperidino-2-hydroxypropyl)nicotinic amidoxime has an insulin sensitizing effect and enhances the effect of antidiabetic and antilipidemic agents on, among others, type II diabetes mellitus (noninsulin-dependent diabetes mellitus, NIDDM) and insulin resistance.

The aim of the invention is to restore or increase the function of the nNOS enzyme by administering a suitable pharmaceutically active agent to the patient being in need thereof.

SUMMARY OF THE INVENTION

It has been found that the above aim can be achieved by a pharmaceutical composition containing O-(3-piperidino-2-hydroxypropyl)nicotinic amidoxime or a pharmaceutically suitable acid addition salt thereof as the active agent. When the pharmaceutical composition of the invention is administered to patients suffering from diseases that can be characterized by a reduced activity of the nNOS enzyme, surprisingly, their state can be significantly improved.

DESCRIPTION OF PREFERRED EMBODIMENTS

The pharmaceutical composition of the invention is suitable for the treatment of, mainly, the following diseases:

Gastrointestinal motility disorders (e.g. achalasia, obstipation, functional dyspepsia, intestinal pseudoobstruction, infantile hypertrophic pylorus stenosis, biliary diskinesia, reflux esophagitis, gall bladder dysfunction such as reduced flow of bile from the gall bladder, types II and III biliary and pancreatic sorts of sphincter of Oddi dysfunction (SOD), postcholecystectomy syndrome, motility disorders of non-ulcerative colitis, all types of gastroparesis, defecation disturbances and all types of active faecal incontinences etc.).

Hemorrhoids, fissura ani (conservative treatment).

Functional disorders of urinary bladder (e.g. neurogen urinary retention etc.).

Muscle degeneration (e.g. Duchene muscular dystrophy).

Erectile dysfunctions, impaired fertility, traumatic peripheral nerve lesion, nephrosis etc.

The pharmaceutical composition of the invention can be preferably used as a prokinetic agent that induces gastrointestinal activity. For the purposes of the invention, the term "prokinetic effect" includes effects useful in the treatment of the gastrointestinal motility disorders listed above.

O-(3-piperidino-2-hydroxy-1-propyl)nicotinic amidoxime can be prepared according to the process described in U.S. Pat. No. 6,306,878. A salt formed with an inorganic acid such as hydrochloric acid, sulfuric acid etc. or with an organic acid such as acetic acid, lactic acid, tartaric acid etc. can be used as a pharmaceutically suitable acid addition salt. Preferred acid addition salt of O-(3-piperidino-2-hydroxy-1-propyl)nicotinic amidoxime is the dihydrochloride thereof.

The effect of 0-(3-piperidino-2-hydroxy-1-propyl)nicotinic amidoxime on the function of the nNOS enzyme was investigated in the following tests.

1. Effect on the Cellular Expression of nNOS 1.1 The in vitro test was carried out in rat brain capillary endothelial cells. The rat brain capillary endothelial cells were grown in F12 medium (GibcoBRL, Eggenstein, Germany) supplemented with 10% of fetal calf serum (FCS) (GibcoBRL, Eggenstein, Germany), penicillin (400 IU/ml), streptomycin (50 .mu.g/ml) and glutamine (2 mM). The cell culture was grown at 37.degree. C. under an atmosphere consisting of 5% of carbon dioxide and 95% of air. To achieve a constant normoglycaemic state, a glucose concentration of 5 mM was maintained by changing the medium on every second day and continuously controlling the glucose level. The cells were regularly passed twice weekly. For each experiment a confluent culture forming a continuous cell layer was used. To the cell cultures, O-(3-piperidino-2-hydroxypropyl)nicotinic amidoxime was added as the dihydrochloride in a concentration of 10, 30 and 100 .mu.M, respectively, (the compound is also mentioned in the description as ("BGP-15"), and the effect of the treatment was examined after 3, 6 and 24 hours. At the end of the treatment, the cells were collected and Western blot analysis was performed as follows:

The cells were rinsed and collected in ice-cold PBS (phosphate buffer in physiological saline) (pH=7.4) containing 5 mM of ethylenediaminetetraacetic acid (EDTA), 5 mM of sodium fluoride and 100 µM of $Na_3VO_4$. Lysis of the cell pellet was carried out on ice under weak shaking for 10 minutes in a buffer solution containing 250 mM of sodium chloride, 50 mM of HEPES [4-(2-hydroxyethyl)-1-piperazineethanesulfonic acid] (pH=7.4), 1 mM of EDTA, 1 mM of EGTA [ethyleneglycol-bis(2-aminoethyl ether)-N,N,N',N'-tetraacetic acid], 1.5 mM of magnesium chloride, 0.1% of Nonidet P-40, 40 mM of β-glycerol phosphate, 1 mM of $Na_3VO_4$, 1 mM of phenylmethylsulfonyl fluoride, 10 mM of benzamidine, 20 mM of NaF, 10 mM of sodium pyrophosphate, 10 µM/ml of aprotinin, 10 µg/ml of leupeptin, and 10 µg/ml of antipain. The insoluble cell debris was removed by centrifugation (13000 g, 12 minutes, +4° C.). The clear supernatant was admixed to ½ volume of 2× Laemmli gel loading buffer, the samples were boiled for 3 minutes, then maintained at −20° C. before use. The protein concentration was determined by means of Bio-Rad $D_c$ Protein Assay reagent (Bio-Rad Laboratories, Hercules, Calif., USA). Samples containing identical amount of protein were separated by polyacrylamide gel electrophoresis in the presence of 10% of sodium dodecylsulfate (10% SDS-PAGE) and blotted on PVDF membrane using a Trans-Blot SD Blotting Kit (Bio-Rad Laboratories). The immune detection of neuronal nitric oxide synthase enzyme was carried out by means of monoclonal anti-nNOS antibody (Transduction Laboratories). Anti-mouse IgG HRP conjugated antibody (Cell Signalling Technologies) was used as secondary antibody. For the detection, ECL Plus System (Amersham) was used. The spots formed were measured by densitometry to obtain optical density values which were averaged. The higher are the area and optical density of the spot, the higher is the concentration of the nNOS enzyme formed. The results obtained are shown in Table 1.

TABLE 1

In vitro test of the formation of neuronal nitric oxide synthase enzyme

| Time after treatment in hours | Rate of formation of nNOS enzyme based on optical density in the presence of | | |
|---|---|---|---|
| | 10 µM of BGP-15 | 30 µM of BGP-15 | 100 µM of BGP-15 |
| 0 | 1 | 1 | 1 |
| 3 | 3.0 | 9.2 | 9.5 |
| 6 | 7.5 | 6.9 | 10.2 |
| 24 | 5.0 | 12.5 | 9.8 |

From the data of Table 1 it is evident that treatment with the compound "BGP-15" induces the formation of neuronal nitric oxide synthase enzyme in rat brain capillary endothelial cells in the concentration range of 10-100 .mu.M. In the presence of 30-100 .mu.M of the compound tested, the amount of enzyme increased after already 3 hours significantly i.e. to a multiple of the starting value, and it did not diminish considerably even after 24 hours. Moreover, in case of 30 .mu.M of "BGP-15", the amount of the enzyme is still higher after 24 hours.

1.2 The in vitro tests described under 1.1 were repeated using PC 12 cell line which was grown, treated with compound "BGP-15" in a concentration of 1, 10 and 100 .mu.M, respectively, and Western blot analysis was carried out as described above. The results expressed as optical density values are shown in Table 2.

TABLE 2

The amount of neuronal nitric oxide synthase enzyme on PC12 cell line

| Time after treatment in hours | Amount of nNOS enzyme based on optical density in the presence of | | |
|---|---|---|---|
| | 1 µM of BGP-15 | 10 µM of BGP-15 | 100 µM of BGP-15 |
| 0 | 1 | 1 | 1 |
| 3 | 3.7 | 8.9 | 13.9 |

The data of Table 2 referring to PC 12 cell line confirm the observations obtained in rat brain capillary endothelial cells that the compound "BGP-15" induced the increased formation of neuronal nitric oxide synthase enzyme in a concentration range of 1-100 .mu.M. After 3 hours, the amount of nNOS enzyme was 3.7-13.9 times the starting value.

2. Tests on Gastrointestinal Smooth Muscle Preparations of Rabbit 2.1 Tests on Biliary Sphincter of Oddi Muscle Rings Using Cholecystokinin Octapeptide and Compound "BGP-15"

Cholecystokinin octapeptide (CCK-8) is a polypeptide secreted by the cells of duodenum in response to the presence of partly digested food in the duodenum. CCK-8 causes through the operation of the sphincter of Oddi (a muscle ring surrounding the orifice of the gall bladder) a flow of bile into the intestine for the digestion of food. In our experiments the effect of CCK-8, compound "BGP-15" and the combination thereof on the contraction of sphincter of Oddi rings isolated from rabbit was investigated.

The sphincter of Oddi was removed from adult male New Zealand white rabbits weighing 3.5-4 kg, and muscle ring of about 3 mm width were prepared. Each of the rings was mounted horizontally on two small L-shaped glass hooks, one of which was connected to a force transducer (SG-02, Experimetria, Budapest, Hungary) attached to a six-channel polygraph ((R61 6CH, Mikromed, Budapest, Hungary) for measurement and recording of isometric tension. The experiments were carried out in an organ bath of 5 ml volume containing Krebs bicarbonate buffer (118.1 mM of sodium chloride, 4.7 mM of potassium chloride, 1.0 mM of magnesium sulfate, 1.0 mM of potassium dihydrogen phosphate, 0.5 mM of calcium chloride, 25.0 mM of sodium hydrogen carbonate and 11.1 mM of glucose). The organ bath was maintained at 37° C. and aerated continuously with carbogen (5% of carbon dioxide in oxygen according to European Pharmacopoeia, Edition III). The initial tension was set to 10 mN and the rings were allowed to equilibrate over 1 hour.

In case of each test type, 6 parallel experiments were carried out, and the average of the results obtained was determined. The following test types were made:
treatment with cholecystokinin octapeptide to simulate the effect existing in the living organism,
pretreatment with the compound "BGP-15" for 5 days, then treatment with cholecystokinin octapeptide,
treatment with the compound "BGP-15",
treatment with organ bath (control group).

In case of using the compound "BGP-15" alone, the rings were exposed to a daily dose of 20 mg/kg of the compound for 5 days. In the treatment with cholecystokinin octapeptide, $5 \times 10^{-7}$ M of the polypeptide was employed. In case of the treatment with both agents, the muscle rings were exposed to a daily dose of 20 mg/kg of "BGP-15" for 5 days, followed by one treatment with $5 \times 10^{-7}$ M of cholecystokinin octapeptide on the fifth day. The results obtained are given in Table 3.

TABLE 3

Effect of the sphincter of Oddie muscle rings

| Parameter examined | Control | BGP-15 20 mg/kg | CCK-8 $5 \times 10^{-7}$ M | BGP-15 + CCK-8 |
|---|---|---|---|---|
| Max. contraction in mN | 16 | 18 | 29 | 35 |
| Max. relaxation in mN | 0 | 0 | 5 | 8 |
| Frequency of contraction in c/min. | 13 | 13 | 19 | 22 |
| Max. tonic contraction in mN | 10 | 10 | 24 | 28 |

From Table 3 it can be seen that a treatment period for 5 days with the compound "BGP-15" alone causes only a small change relative to the control group. However, when the samples pretreated with the compound "BGP-15" for 5 days were exposed to cholecystokinin octapeptide, each of the parameters examined increased relative to the data obtained in the treatment with "BGP-15" alone or CCK-8 alone. It is noteworthy that in case of the combined treatment, the maximum contraction is about 20%, the maximum relaxation is about 60% higher than the value obtained in the treatment with CCK-8 alone.

2.2 Tests Using Electrical Field Stimulation

The sphincter of Oddi, oesophagus sphincter, taeniae coli and internal anal sphincter were removed from adult male New Zealand white rabbits weighing 3.5-4 kg. From the sphincters, muscle ring slices of about 3 mm width, from the taeniae coli, muscle preparations of approximately 6 mm length were prepared. The organ preparations were tested using the organ bath and experimental arrangement described under 3.1 above. At an initial tension of 10 mN, the electrical field stimulation had the following characteristics: 100 stimuli at 20 V, 0.1 ms and 20 Hz.

In case of each test type, 6 parallel experiments were carried out, and the average of the results obtained was determined. The following test types were made:
determination of the maximum contraction with an organ bath (control) treatment,
determination of the maximum contraction following a treatment with a daily dose of 20 mg/kg of the compound "BGP-15" for 5 days,
determination of the maximum relaxation under non-adrenergic, non-cholinergic (NANC) conditions (in the presence of 1 .mu.M of atropine and 4 .mu.M of guanethidine [[2-(hexahydro-1-(2H)-azocinyl)ethyl]guanidine]), (control),
determination of the maximum relaxation under non-adrenergic, non-cholinergic (NANC) conditions (in the presence of 1 .mu.M of atropine and 4 .mu.M of guanethidine after a pretreatment with a daily dose of 20 mg/kg of "BGP-15" for 5 days.

The results obtained are shown in Table 4.

TABLE 4

Electric field stimulation on various organ samples

| Organ tested | Max. contraction in mN | | Max. relaxation in mN NANC | |
|---|---|---|---|---|
| | Control | BGP-15 | control | BGP-15 |
| Sphincter of Oddi | 23 | 29 | 4 | 8 |
| Oesophagus sphincter | 16 | 27 | 4 | 7 |
| Taeniae coli | 22 | 26 | 3 | 5 |
| Internal anal sphincter | 21 | 29 | 4 | 6 |

The data of Table 4 indicate that the contraction and relaxation of each organ tested is favourably influenced by the pretreatment with the compound "BGP-15".

Based on the contractile and relaxant effect of the compound "BGP-15", wherein the effect was exerted on the sphincter of Oddi, the pharmaceutical composition of the invention could be used to increase the bile flow, to treat the motility disorders of the bile duct as well as the postcholecystectomy syndrome that develops following the removal of the gall bladder owing to the ceasing of the Wyatt's reflex. From the contractile and relaxant effect of "BGP-15" exerted on the oesophagus sphincter it follows that the pharmaceutical composition of the invention can be also used for the treatment of the disease reflux esophagitis. Due to the contractile and relaxant effect of "BGP-15" exerted on the internal anal sphincter and taeniae coli, the pharmaceutical composition of the invention can be used to increase the motility of the intestine.

The pharmaceutical composition employed according to the invention may include any dosage form, however, it is suitable, primarily, for peroral administration, and can be solid or liquid.

The solid pharmaceutical compositions suitable for peroral administration may be powders, capsules, tablets, film-coated tablets, microcapsules etc., and can comprise binding agents such as gelatine, sorbitol, poly(vinylpyrrolidone) etc.; filling agents such as lactose, glucose, starch, calcium phosphate etc.; auxiliary substances for tabletting such as magnesium stearate, talc, poly(ethylene glycol), silica etc.; wetting agents such as sodium laurylsulfate etc. as the carrier.

The liquid pharmaceutical compositions suitable for peroral administration may be solutions, suspensions or emulsions and can comprise e.g. suspending agents such as gelatine, carboxymethylcellulose etc.; emulsifiers such as sorbitane monooleate etc.; solvents such as water, oils, glycerol, propylene glycol, ethanol etc.; preservatives such as methyl p-hydroxybenzoate etc. as the carrier.

The pharmaceutical composition contains dosage unit, in general. A typical dose for adult patients amounts to 0.1 to 1000 mg, preferably 1 to 250 mg of O-(3-piperidino-2-hydroxypropyl)nicotinic amidoxime or a pharmaceutically suitable acid addition salt thereof calculated for 1 kg body weight, daily. The daily dose can be administered in one or more portions. The actual dosage depends on many factors and is determined by the doctor.

The pharmaceutical composition is prepared by admixing the O-(3-piperidino-2-hydroxypropyl)nicotinic amidoxime or a pharmaceutically suitable acid addition salt thereof to one or more pharmaceutical carrier(s) and transforming the mixture obtained into a pharmaceutical composition in a manner known per se.

Dosage forms listed above as well as other dosage forms, the manufacture thereof and pharmaceutical carriers are known from the literature, see e.g. Remington's Pharmaceutical Sciences, 18th Edition, Mack Publishing Co., Easton, USA (1990).

The invention includes also a method for restoring and/or increasing the activity of the neuronal nitric oxid synthase enzyme in a mammal including man in which the patient being in need thereof is treated with a therapeutically effective non-toxic amount of O-(3-piperidino-2-hydroxypropyl) nicotinic amidoxime or a pharmaceutically suitable acid addition salt thereof.

The invention claimed is:

1. A method of treating gastrointestinal motility disorders in a subject in need thereof which comprises:
   administering therapeutically effective amount of O-(3-piperidino-2-hydroxypropyl) nicotinic amidoxime or a pharmaceutically suitable acid addition salt thereof,
   wherein the gastrointestinal motility disorders are selected from the group consisting of reflux esophagitis, type II biliary and pancreatic sphincter of Oddi dysfunction, type III biliary and pancreatic sphincter of Oddi dysfunction, postcholecystectomy syndrome, non-ulcerative colitis, defecation disturbances and fecal incontinences.

2. The method according to claim 1, wherein the gastrointestinal motility disorder is reflux esophagitis.

3. The method according to 1, wherein the subject in need thereof is in need of enhancement of the flow of bile from the gall bladder.

4. The method according to claim 1, wherein the gastrointestinal motility disorder is types II or III biliary and pancreatic sphincter of Oddi dysfunction.

5. The method according to claim 1, wherein the gastrointestinal motility disorder is postcholecystectomy syndrome.

6. The method according to claim 1, wherein the gastrointestinal motility disorder is non-ulcerative colitis.

7. The method according to claim 1, wherein the gastrointestinal motility disorder is defecation disturbances or fecal incontinences.

* * * * *